United States Patent
Okano et al.

(10) Patent No.: US 11,850,084 B2
(45) Date of Patent: Dec. 26, 2023

(54) FRACTURE RISK EVALUATION VALUE ACQUISITION DEVICE, METHOD FOR OPERATING FRACTURE RISK EVALUATION VALUE ACQUISITION DEVICE, AND NON-TRANSITORY COMPUTER READABLE MEDIUM

(71) Applicant: FUJIFILM Corporation, Tokyo (JP)

(72) Inventors: Kayo Okano, Kanagawa (JP); Takahiro Kawamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 394 days.

(21) Appl. No.: 17/399,776

(22) Filed: Aug. 11, 2021

(65) Prior Publication Data
US 2021/0369224 A1 Dec. 2, 2021

Related U.S. Application Data

(63) Continuation of application No. PCT/JP2020/005141, filed on Feb. 10, 2020.

(30) Foreign Application Priority Data

Feb. 14, 2019 (JP) .................................. 2019-024092

(51) Int. Cl.
*A61B 6/00* (2006.01)
*G16H 50/30* (2018.01)
*G16H 30/40* (2018.01)

(52) U.S. Cl.
CPC ............. *A61B 6/505* (2013.01); *G16H 30/40* (2018.01); *G16H 50/30* (2018.01)

(58) Field of Classification Search
CPC .......... A61B 6/505; G16H 50/30; G16H 30/40
See application file for complete search history.

(56) References Cited

U.S. PATENT DOCUMENTS

| 2004/0059223 | A1  | 3/2004 | Faulkner et al. |
| 2004/0077088 | A1* | 4/2004 | Charles Jr. ............. A61B 6/467 435/455 |

(Continued)

FOREIGN PATENT DOCUMENTS

| JP | H06-22960 A    | 2/1994 |
| JP | 2004-105738 A  | 4/2004 |

(Continued)

OTHER PUBLICATIONS

An Office Action; "Decision of Refusal", mailed by the Japanese Patent Office dated Jan. 31, 2023, which corresponds to Japanese Patent Application No. 2020-572246 and is related to U.S. Appl. No. 17/399,776; with English language translation.

(Continued)

*Primary Examiner* — Hugh Maupin
(74) *Attorney, Agent, or Firm* — Studebaker & Brackett PC

(57) ABSTRACT

A subject information acquisition unit calculates a bone mineral density in the bone region and a muscle mass in the soft region for each pixel on the basis of a radiographic image. A statistical value calculation unit calculates a statistical value related to the subject on the basis of the bone mineral density and the muscle mass. An evaluation value calculation unit calculates the fracture risk evaluation value for evaluating the fracture risk of the subject on the basis of the statistical value.

12 Claims, 7 Drawing Sheets

(56) References Cited

U.S. PATENT DOCUMENTS

2014/0185902 A1    7/2014  Wilson
2020/0060636 A1*  2/2020  Wilson .................... A61B 6/50
2020/0167921 A1*  5/2020  Kelly .................... G06T 7/0012

FOREIGN PATENT DOCUMENTS

| JP | 2009-515594 A | 4/2009 |
| JP | 2011-045480 A | 3/2011 |
| WO | 2016/190327 A1 | 12/2016 |

OTHER PUBLICATIONS

International Search Report issued in PCT/JP2020/005141; dated Apr. 14, 2020.
International Preliminary Report on Patentability and Written Opinion issued in PCT/JP2020/005141; dated Aug. 10, 2021.
An Office Action; "Notice of Reasons for Refusal," mailed by the Japanese Patent Office dated Aug. 9, 2022, which corresponds to Japanese Patent Application No. 2020-572246 and is related to U.S. Appl. No. 17/399,776; with English language translation.

* cited by examiner

FRACTURE RISK EVALUATION VALUE ACQUISITION DEVICE, METHOD FOR OPERATING FRACTURE RISK EVALUATION VALUE ACQUISITION DEVICE, AND NON-TRANSITORY COMPUTER READABLE MEDIUM

CROSS-REFERENCE TO RELATED APPLICATIONS

This application is a Continuation of PCT International Application No. PCT/JP2020/005141 filed on 10 Feb. 2020, which claims priority under 35 U.S.C § 119(a) to Japanese Patent Application No. 2019-024092 filed on 14 Feb. 2019. The above application is hereby expressly incorporated by reference, in its entirety, into the present application.

BACKGROUND OF THE INVENTION

1. Field of the Invention

The present invention relates to a fracture risk evaluation value acquisition device, a method for operating a fracture risk evaluation value acquisition device, and a non-transitory computer readable medium that calculate an evaluation value for evaluating a fracture risk.

2. Description of the Related Art

In the medical field, diagnosis using radiographic images is performed. In the diagnosis using the radiographic images, in addition to the radiographic images, various kinds of information obtained from the radiographic images are used. Various kinds of information used for diagnosing radiographic images include an evaluation value for evaluating a fracture risk.

In JP1994-22960A (JP-H06-22960A), bone mineral density (BMD) is measured using X-rays, and bone density is calculated from the bone mineral density (BMD) per osteon and the thickness of bone. Then, an evaluation value for evaluating the fracture risk is calculated from an ultrasound propagation velocity V in the bone and the bone density.

SUMMARY OF THE INVENTION

However, the fracture risk does not depend on only the factors of a bone part, such as bone mineral density, and is greatly affected by factors related to a soft part other than the bone part, such as muscle mass. In addition, in a case in which the fracture risk is accurately calculated, it is preferable to calculate the evaluation value not using, for example, the bone mineral density of the osteon but using the bone mineral density calculated for each pixel of the bone such as a bone part.

An object of the invention is to provide a fracture risk evaluation value acquisition device, a method for operating a fracture risk evaluation value acquisition device, and a non-transitory computer readable medium that can calculate a fracture risk evaluation value for evaluating a fracture risk using information of the entire subject including a bone region and a soft region.

According to the invention, there is provided a fracture risk evaluation value acquisition device comprising a processor. The processor acquires a radiographic image obtained by capturing an image of a subject including a bone part and a soft part, specifies a bone region indicating a region of the bone part and a soft region indicating a region of the soft part from the radiographic image, calculates a bone mineral density in the bone region and a muscle mass in the soft region for each pixel on the basis of the radiographic image, calculates a statistical value related to the subject on the basis of the bone mineral density and the muscle mass, and calculates a fracture risk evaluation value for evaluating a fracture risk of the subject on the basis of the statistical value.

Preferably, the processor calculates the statistical value on the basis of a bone mineral density distribution index value related to a spatial distribution of the bone mineral density and a muscle mass distribution index value related to a spatial distribution of the muscle mass. Preferably, the bone mineral density distribution index value is any one of a value of the bone mineral density per unit area or an average value, an intermediate value, a maximum value, or a minimum value of the bone mineral density, and the muscle mass distribution index value is any one of an average value, an intermediate value, a maximum value, or a minimum value of the muscle mass.

Preferably, the processor calculates the statistical value on the basis of at least one of a height, a weight, an age, or a fracture history of the subject in addition to the bone mineral density and the muscle mass. Preferably, the processor issues a warning in a case in which the fracture risk evaluation value is greater than a risk threshold value. Preferably, the processor calculates the bone mineral density on the basis of a body thickness distribution of the subject, a pixel value of the bone region, and imaging conditions in a case in which the body thickness distribution and the radiographic image are acquired. Preferably, the processor calculates the bone mineral density by multiplying the pixel value of the bone region by a conversion coefficient based on the body thickness distribution and the imaging conditions.

Preferably, the processor calculates the muscle mass for each pixel, using a body thickness distribution of the subject and a pixel value of the soft region. Preferably, the processor calculates the muscle mass on the basis of a predetermined specific relationship between the body thickness distribution and the pixel value of the soft region. Preferably, the specific relationship changes depending on the imaging conditions at a timing when the image of the subject is captured.

According to the invention, there is provided a method for operating a fracture risk evaluation value acquisition device. The method includes processor implemented steps of: acquiring a radiographic image obtained by capturing an image of a subject including a bone part and a soft part; specifying a bone region indicating a region of the bone part and a soft region indicating a region of the soft part from the radiographic image; calculating a bone mineral density in the bone region and a muscle mass in the soft region for each pixel on the basis of the radiographic image; calculating a statistical value related to the subject on the basis of the bone mineral density and the muscle mass; and calculating a fracture risk evaluation value for evaluating a fracture risk of the subject on the basis of the statistical value.

According to the invention, there is provided a non-transitory computer readable medium for storing a computer-executable program for causing a computer to perform steps of: acquiring a radiographic image obtained by capturing an image of a subject including a bone part and a soft part; specifying a bone region indicating a region of the bone part and a soft region indicating a region of the soft part from the radiographic image; calculating a bone mineral density in the bone region and a muscle mass in the soft region for each pixel on the basis of the radiographic image; calculating a statistical value related to the subject on the basis of the bone mineral density and the muscle mass; and calculating a fracture risk evaluation value for evaluating a fracture risk of the subject on the basis of the statistical value.

According to the invention, it is possible to calculate the fracture risk evaluation value for evaluating the fracture risk using the information of the entire subject including the bone region and the soft region.

DESCRIPTION OF THE PREFERRED EMBODIMENTS

Figure 1:
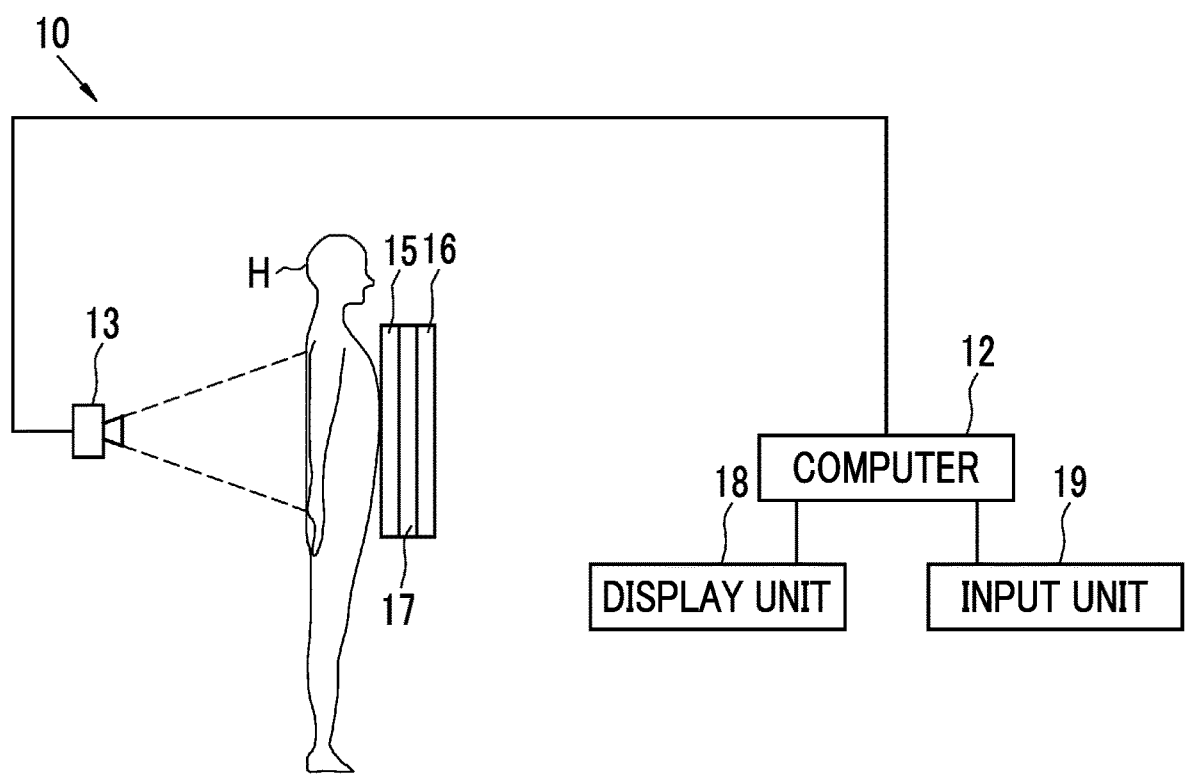
FIG. 1 is a diagram schematically illustrating a configuration of a radiography system.

As illustrated in FIG. 1, a radiography system comprises an imaging apparatus 10 and a computer 12 and captures two radiographic images having different energy distributions. In the imaging apparatus 10, in a case in which a first radiation detector 15 and a second radiation detector 16 receive X-rays that have been emitted from an X-ray source 13 which is a radiation source and then transmitted through a subject H, the first radiation detector 15 and the second radiation detector 16 receive the X-rays while changing energy (one-shot energy subtraction). At the time of imaging, the first radiation detector 15, an X-ray energy conversion filter 17 that consists of, for example, a copper plate and the second radiation detector 16 are disposed in this order from the side closer to the X-ray source 13, and the X-ray source 13 is driven. In addition, the first and second radiation detectors 15 and 16 and the X-ray energy conversion filter 17 come into close contact with each other.

Therefore, the first radiation detector 15 obtains a first radiographic image G1 of the subject H formed by low-energy X-rays including so-called soft rays. In addition, the second radiation detector 16 obtains a second radiographic image G2 of the subject H formed by high-energy X-rays excluding soft rays. The first and second radiographic images G1 and G2 are input to the computer 12. In this embodiment, in a case in which a scattered ray removal grid that removes scattered ray components of the X-rays transmitted through the subject H is used at the time of capturing the image of the subject H, the first radiographic image G1 and the second radiographic image G2 include primary ray components of the X-rays transmitted through the subject H.

On the other hand, in a case in which the scattered ray removal grid is not used at the time of capturing the image of the subject H, the first and second radiographic images G1 and G2 include primary ray components and scattered ray components of the X-rays.

A so-called direct-type radiation detector that can repeatedly perform the recording and reading of a radiographic image, directly receives the emitted radiation, and generates charge may be used as the first and second radiation detectors 15 and 16. Alternatively, an indirect radiation detector that converts radiation into visible light and then converts the visible light into a charge signal may be used as the first and second radiation detectors 15 and 16. A so-called optical reading method which turns on and off a thin film transistor (TFT) switch to read a radiographic image signal is preferably used as a radiographic image signal reading method.

A display unit 18 and an input unit 19 are connected to the computer 12. The display unit 18 consists of a cathode ray tube (CRT), a liquid crystal display, or the like and displays a radiographic image or the like acquired by imaging. The input unit 19 consists of, for example, a keyboard, a mouse, or a touch panel.

A fracture risk evaluation value acquisition program is installed in the computer 12. In this embodiment, the computer 12 may be a workstation or a personal computer that is directly operated by an operator, or a server computer that is connected to them through a network. The fracture risk evaluation value acquisition program is recorded on a recording medium, such as a digital versatile disc (DVD) or a compact disc read only memory (CD-ROM), is distributed, and is installed in the computer 12 from the recording medium. Alternatively, the subject information acquisition program is stored in a storage device of the server computer connected to the network or a network storage in a state in which it can be accessed from the outside and is downloaded and installed in the computer 12 as required.

Figure 2:
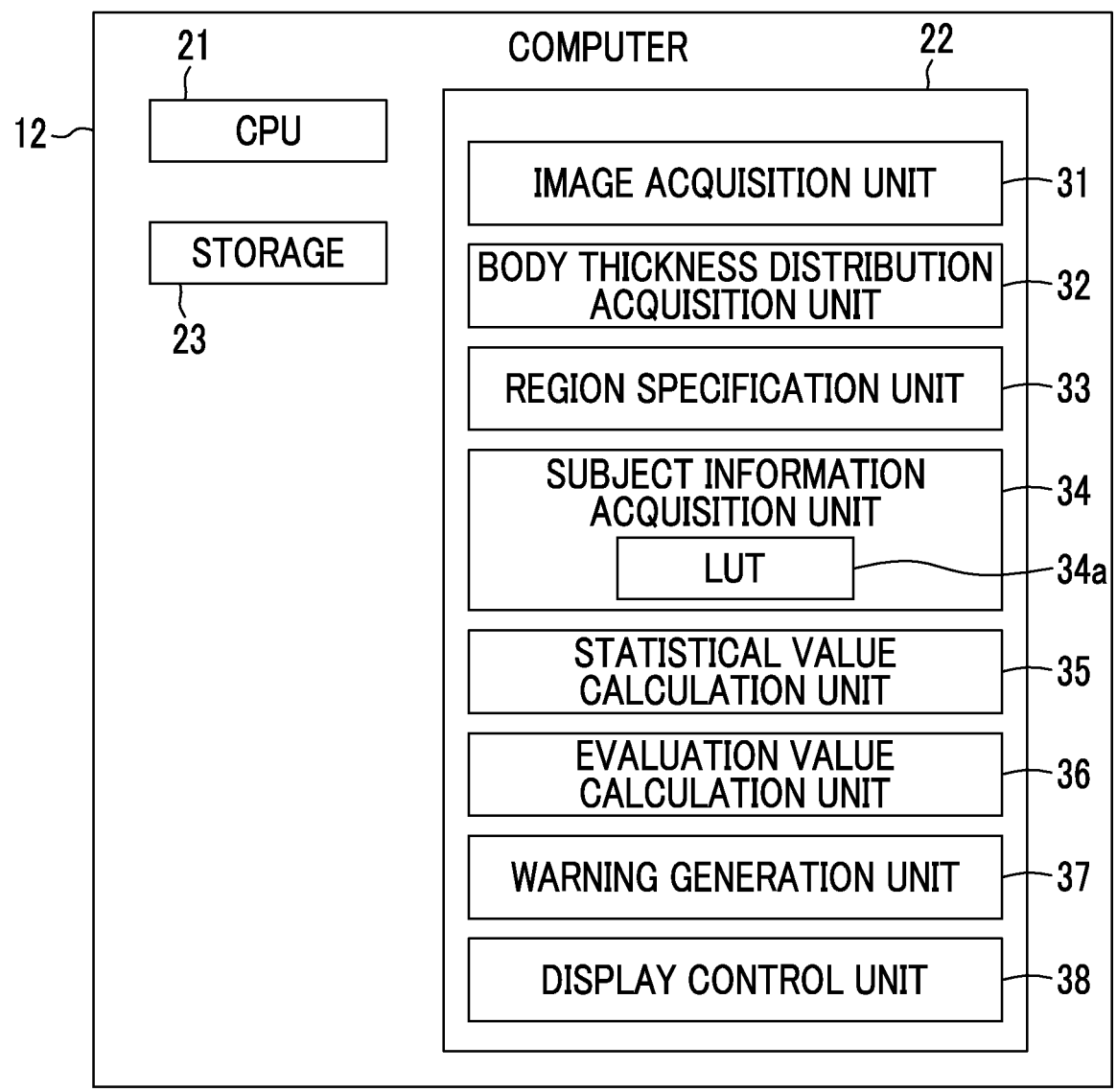
FIG. 2 is a block diagram illustrating the functions of a computer.

FIG. 2 illustrates a schematic configuration of a fracture risk evaluation acquisition device implemented by installing the fracture risk evaluation value acquisition program in the computer 12. The subject information acquisition device comprises a central processing unit (CPU) 21, a memory 22, and a storage 23. The storage 23 consists of a storage device, such as a hard disk or a solid state drive (SSD), and stores various kinds of information including a program for driving each unit of the imaging apparatus 10 and a subject information acquisition program. In addition, the radiographic image acquired by imaging is stored in the storage 23.

The memory 22 temporarily stores, for example, the program stored in the storage 23 in order to cause the CPU 21 to perform various processes. The fracture risk evaluation value acquisition program defines the following processes as the processes to be performed by the CPU 21: an image acquisition process of directing the imaging apparatus 10 to perform imaging and acquiring the first and second radiographic images G1 and G2 as radiographic images; a region specification process of specifying a bone region and a soft region from the radiographic images; a subject information acquisition process of calculating a bone mineral density in the bone region and a muscle mass in the soft region for each pixel; a statistical value calculation process of calculating a statistical value related to the subject on the basis of the bone mineral density and the muscle mass; an evaluation value calculation process of calculating a fracture risk evaluation value for evaluating the fracture risk of the subject on the basis of the statistical value; and a warning generation process of issuing a warning on the basis of the fracture risk evaluation value. In addition, the fracture risk evaluation value acquisition program includes a recognition process for specifying a region which will be described below.

Then, the CPU 21 composed of a processor performs the processes according to the fracture risk evaluation value acquisition program such that the computer 12 functions as an image acquisition unit 31, a body thickness distribution acquisition unit 32, a region specification unit 33, a subject information acquisition unit 34, a statistical value calculation unit 35, an evaluation value calculation unit 36, a warning generation unit 37, and a display control unit 38. In addition, the computer 12 functions as a region recognition processing unit 40 (see FIG. 11). Further, in this embodiment, the CPU 21 implements the functions of each unit according to the fracture risk evaluation value acquisition program. However, in addition to the CPU 21, a programmable logic device (PLD) that is a processor whose circuit configuration can be changed after manufacture, such as a field programmable gate array (FPGA), can be used as a general-purpose processor that executes software to function as various processing units. In addition, the processes of each unit may be performed by, for example, a dedicated electric circuit that is a processor having a dedicated circuit configuration designed to perform a specific process, such as an application specific integrated circuit (ASIC).

One processing unit may be configured by one of the various processors or a combination of two or more processors of the same type or different types (for example, a combination of a plurality of FPGAs or a combination of a CPU and an FPGA). Further, a plurality of processing units may be configured by one processor. A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as the hardware structure.

In addition, specifically, an electric circuit (circuitry) obtained by combining circuit elements, such as semiconductor elements, is used as the hardware structure of the various processors.

The image acquisition unit 31 acquires the first and second radiographic images G1 and G2 obtained by capturing the images of the subject including a bone part and a soft part and detecting the images with the first and second radiation detectors 15 and 16. In this embodiment, the images of the abdomen of the subject H are captured from the chest, and the first and second radiographic images G1 and G2 of the abdomen from the chest are acquired. In this case, imaging conditions, such as an imaging dose, a tube voltage, a source image receptor distance (SID) which is a distance between the X-ray source 13 and the surfaces of the first and second radiation detectors 15 and 16, a source object distance (SOD) which is a distance between the X-ray source 13 and the surface of the subject H, and the presence or absence of the scattered ray removal grid, are set.

The SOD and the SID are used to calculate the body thickness distribution, which will be described below. It is preferable that the SOD is acquired by, for example, a time-of-flight (TOF) camera. It is preferable that the SID is acquired by, for example, a potentiometer, an ultrasonic range finder, or a laser range finder.

It is preferable that the imaging conditions are set by input from the input unit 19 by the operator. The set imaging conditions are stored in the storage 23. In addition, the acquisition program may acquire the first and second radiographic images G1 and G2 using a separate program and store the acquired radiographic images in the storage 23. In this case, the image acquisition unit 31 reads the first and second radiographic images G1 and G2 stored in the storage 23 from the storage 23 in order to process the radiographic images.

The body thickness distribution acquisition unit 32 calculates the body thickness distribution T(x, y) of the subject H on the basis of the SID and the SOD included in the imaging conditions. It is preferable that the body thickness distribution is calculated by subtracting the SOD from the SID. Further, the body thickness distribution is calculated for each pixel corresponding to the first and second radiographic images G1 and G2. Furthermore, instead of calculating the body thickness distribution on the basis of the SID and the SOD, the body thickness distribution may be calculated from at least one of the first radiographic image G1 or the second radiographic image G2. Moreover, the body thickness distribution may be calculated from the soft part image of the subject H obtained by performing weighting and subtraction between the corresponding pixels of the first radiographic image and the second radiographic image. In addition, in the calculation of the body thickness distribution, in a case in which the first and second radiation detectors 15 and 16 are provided in an imaging table (not illustrated) on which the subject H is placed, it is preferable that the distance of the X-ray source 13 to the surface of the imaging table which comes into contact with the subject H is used as the SID.

Figure 3:
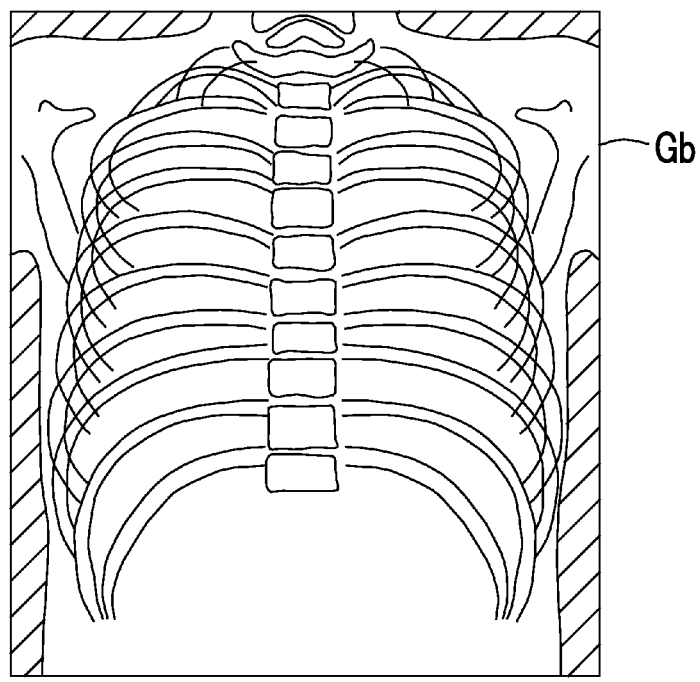
FIG. 3 is an image diagram illustrating a bone part image.

The region specification unit 33 specifies a bone region and a soft region of the subject H from the first and second radiographic images G1 and G2. Specifically, in a case in which a bone region is specified, the region specification unit 33 performs calculation, for example, weighting and subtraction between the corresponding pixels of the first and second radiographic images G1 and G2 as represented by the following Expression (1) to generate a bone part image Gb obtained by extracting only the bone region of the subject H included in each of the radiographic images G1 and G2 as illustrated in FIG. 3 (energy subtraction). In Expression (1), β is a weighting coefficient. In addition, the pixel value of each pixel in the bone region of the bone part image Gb is a bone part pixel value.

$$Gs(x,y) = G1(x,y) - \beta \times G2(x,y) \quad (1)$$

Figure 4:
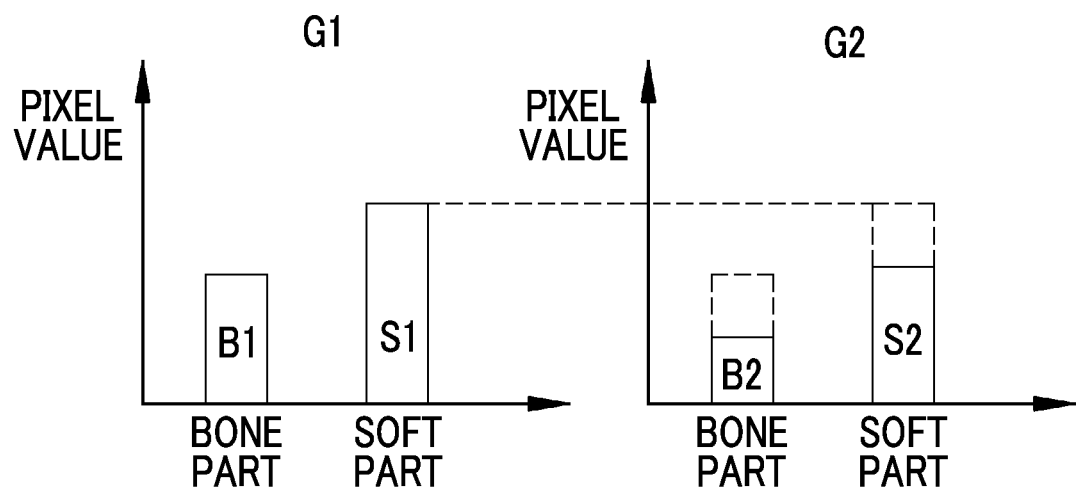
FIG. 4 is a diagram illustrating pixel values of a bone part and a soft part in first and second radiographic images G1 and G2 which are used to obtain a bone region.

For example, in a case in which the pixel value of the bone part and the pixel value of the soft part in the first radiographic image G1 are B1 and S1, respectively, and the pixel value of the bone part and the pixel value of the soft part in the second radiographic image G2 are B2 and S2, respectively, as illustrated in FIG. 4, in the obtainment of the bone part image Gb, the second radiographic image G2 is multiplied by the weighting coefficient β in Expression (1) to make the pixel values of the soft part almost equal to each other in the first radiographic image G1 and the second radiographic image G2. Then, the second radiographic image G2 multiplied by the weighting coefficient is subtracted from the first radiographic image G1 to obtain the bone part image Gb obtained by extracting only the bone part.

Figure 5:
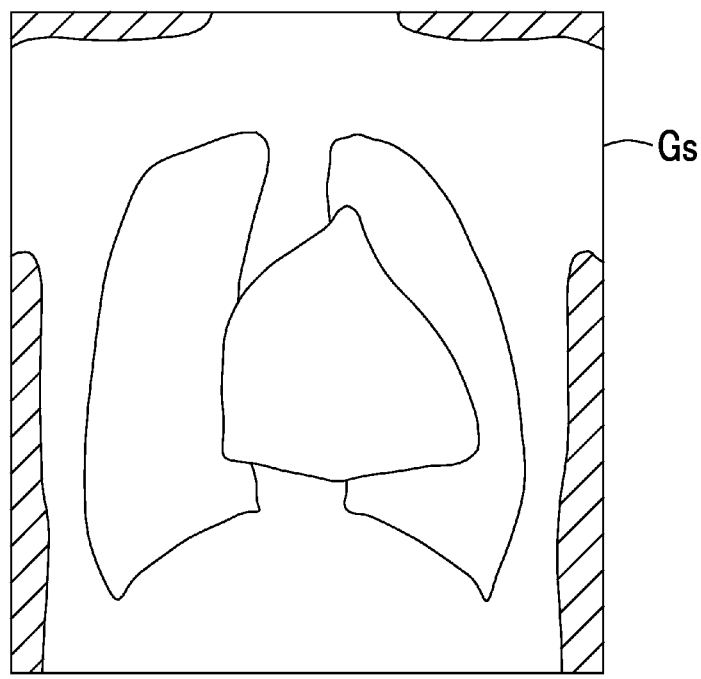
FIG. 5 is an image diagram illustrating a soft part image.

Specifically, in a case in which a soft region is specified, the region specification unit 33 performs calculation, for example, weighting and subtraction between the corresponding pixels of the first and second radiographic images G1 and G2 as represented by the following Expression (2) to generate a soft part image Gs obtained by extracting only the soft region of the subject H included in each of the radiographic images G1 and G2 as illustrated in FIG. 5 (energy subtraction). In Expression (2), μ is a weighting coefficient. In addition, the pixel value of each pixel in the soft region of the soft part image Gs is a soft part pixel value.

$$Gs(x,y)=G1(x,y)-\mu \times G2(x,y) \qquad (2)$$

Figure 6:
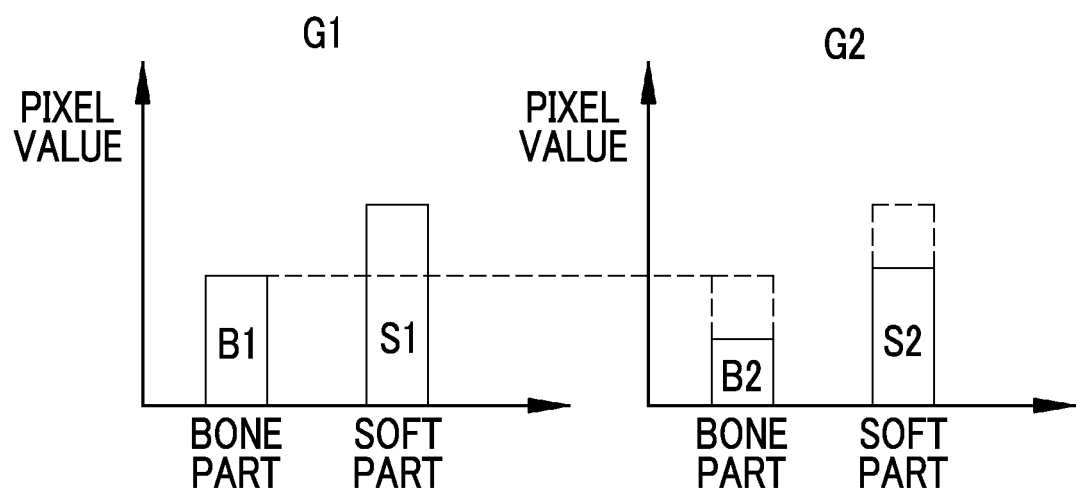
FIG. 6 is a diagram illustrating the pixel values of the bone part and the soft part in the first and second radiographic images G1 and G2 which are used to obtain a soft region.

For example, in a case in which the pixel value of the bone part and the pixel value of the soft part in the first radiographic image G1 are B1 and S1, respectively, and the pixel value of the bone part and the pixel value of the soft part in the second radiographic image G2 are B2 and S2, respectively, as illustrated in FIG. 6, in the obtainment of the soft part image Gs, the second radiographic image G2 is multiplied by the weighting coefficient μ in Expression (2) to make the pixel values of the bone part almost equal to each other in the first radiographic image G1 and the second radiographic image G2. Then, the second radiographic image G2 multiplied by the weighting coefficient is subtracted from the first radiographic image G1 to obtain the soft part image Gs obtained by extracting only the soft part.

The subject information acquisition unit 34 calculates a bone mineral density in the bone region and a muscle mass in the soft region for each pixel. In a case in which the bone mineral density is calculated, the subject information acquisition unit 34 calculates the bone mineral density on the basis of the body thickness distribution, the pixel value of the bone region, and the imaging conditions in a case in which the body thickness distribution and the radiographic images are acquired. Specifically, the subject information acquisition unit 34 acquires a conversion coefficient Cb(x, y) for converting the pixel value of the bone region into the bone mineral density for each pixel with reference to a look-up table (LUT) 34a. The conversion coefficient Cb(x, y) is determined on the imaging conditions and the body thickness distribution T(x, y). Then, as represented by the following Expression (3), the pixel value Gb(x, y) of each pixel in the bone region is multiplied by the conversion coefficient Cb(x, y) to acquire the bone mineral density B(x, y) for each pixel in the bone region.

$$B(x,y)=Cb(x,y) \times Gb(x,y) \qquad (3)$$

Figure 7:
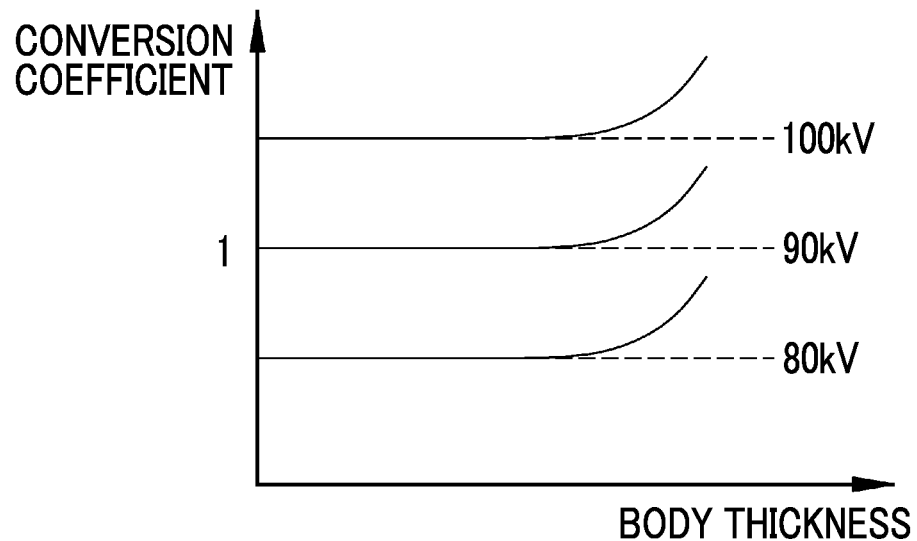
FIG. 7 is a graph illustrating a relationship between a body thickness and a conversion coefficient.

As illustrated in FIG. 7, the LUT 34a defines the relationship between the body thickness included in the body thickness distribution and the conversion coefficient Cb(x, y). As illustrated in the relationship, as the tube voltage included in the imaging conditions becomes higher and the body thickness becomes larger, the value of the conversion coefficient becomes larger. In this embodiment, in a case in which the imaging conditions are the reference imaging conditions, the pixel value of the bone region is equal to the bone mineral density. Therefore, in a case in which the tube voltage in the imaging conditions is a tube voltage of 90 kV which is a reference imaging condition and the body thickness is "0", the conversion coefficient Cb(x, y) is "1".

On the other hand, in a case in which the tube voltage in the imaging conditions is a tube voltage of 100 kV which is greater than the reference imaging condition and the body thickness is "0", the conversion coefficient Cb(x, y) is greater than "1". This is because the contrast of the bone part and the soft part becomes lower as the tube voltage becomes higher. In this embodiment, the pixel value of the bone part is corrected using the conversion coefficient for a decrease in the contrast. On the other hand, in a case in which the tube voltage in the imaging conditions is a tube voltage of 80 kV which is lower than the reference imaging condition and the body thickness is "0", the conversion coefficient Cb(x, y) is less than "1". This is because the contrast of the bone part and the soft part becomes higher as the tube voltage becomes lower. In this embodiment, the pixel value of the bone part is corrected using the conversion coefficient for an increase in the contrast.

In a case in which the muscle mass is calculated, the subject information acquisition unit 34 calculates the muscle mass on the basis of the body thickness distribution and the pixel value of the soft region. Specifically, the subject information acquisition unit 34 calculates the muscle mass on the basis of a predetermined specific relationship based on the body thickness distribution and the pixel value of the soft region. In addition, it is preferable that the specific relationship is stored by, for example, a look-up table (LUT).

Figure 8:
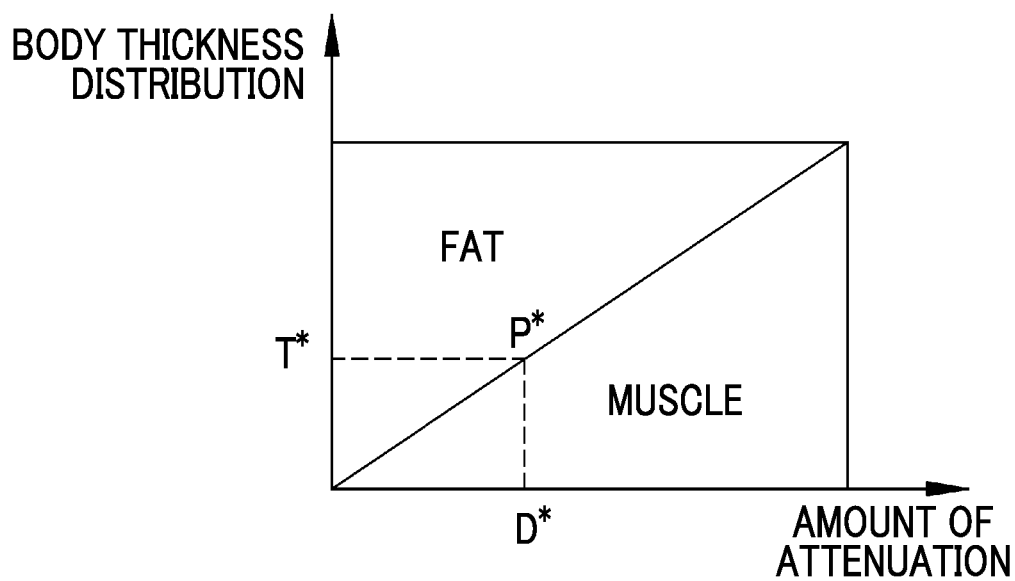
FIG. 8 is a diagram illustrating a specific relationship.

For example, in a case in which the body thickness distribution is represented by the vertical axis and the amount of attenuation (1/(the pixel value of the soft region)) indicating the reciprocal of the pixel value of the soft region is represented by the horizontal axis, the proportion P(x, y) of muscle and fat is determined as the specific relationship, as illustrated in FIG. 8. The proportion P is between "0" and "1". As the proportion P becomes higher, the proportion of muscle becomes higher. For example, in a case in which the body thickness of the body thickness distribution is T* and the amount of attenuation is D*, a proportion P* is used. Then, in a case in which a muscle mass M(x, y) is calculated, the muscle mass M(x, y) is obtained by multiplying the pixel value Gs(x, y) of the soft region by the proportion P as represented by the following Expression (4).

$$M(x,y)=P(x,y) \times Gs(x,y) \qquad (4)$$

For the specific relationship, as the body thickness distribution becomes larger, the proportion of fat becomes higher than the proportion of muscle. This takes advantage of the fact that the body thickness and fat are proportional to each other. In addition, as the amount of attenuation becomes larger, the proportion of muscle becomes higher than the proportion of fat. This takes advantage of the fact that the amount of attenuation of X-rays in muscle is larger than the amount of attenuation of X-rays in fat.

Further, it is preferable to change the specific relationship depending on the imaging conditions obtained at the timing when the image of the subject is captured, that is, the timing when the first radiographic image G1 or the second radiographic image G2 is acquired. For example, the amount of attenuation of X-rays in fat and muscle is changed by a change in the tube voltage or the dose of X-rays among the imaging conditions. Therefore, it is preferable to change the specific relationship according to a change in, for example, the tube voltage or the dose of X-rays. In a case in which the specific relationship is stored in the LUT, it is preferable to determine the specific relationship for each imaging condition.

The statistical value calculation unit 35 calculates a statistical value related to the subject on the basis of the bone mineral density and the muscle mass. The statistical value is used to calculate the fracture risk evaluation value for evaluating the fracture risk, which will be described below. Specifically, as represented by the following Expression (5), the statistical value calculation unit 35 calculates a statistical value I on the basis of a bone mineral density distribution index value Bd related to the spatial distribution of the bone mineral density and a muscle mass distribution index value Md related to the spatial distribution of the muscle mass.

$$I = C1 \times Bd + C2 \times Md \quad (5)$$

In Expression (5), C1 and C2 are weighting coefficients and are determined by collecting a large number of bone mineral density distribution index values and muscle mass distribution index values and performing regression analysis.

The bone mineral density distribution index value is a value indicating how the value of the bone mineral density spreads. Examples of the bone mineral density distribution index value include the value of the bone mineral density per unit area, and the average value, intermediate value, maximum value, and minimum value of the bone mineral density. The muscle mass distribution index value is a value indicating how the value of the muscle mass spreads. Examples of the muscle mass distribution index value include the average value, intermediate value, maximum value, and minimum value of the muscle mass.

Further, the statistical value calculation unit 35 may calculate the statistical value on the basis of at least one of, for example, the height, weight, age, or fracture history of the subject, in addition to the bone mineral density and the muscle mass. For example, in a case in which the statistical value is calculated on the basis of the bone mineral density, the muscle mass, and age, the statistical value I is calculated by the following Expression (6) on the basis of the bone mineral density distribution index value Bd, the muscle mass distribution index value Md, and age Y.

$$I = C1 \times Bd + C2 \times Md + C3 \times Y \quad (6)$$

In Expression (6), C1, C2, and C3 are weighting coefficients. The weighting coefficients C1, C2, and C3 are determined by collecting a large amount of data related to the bone mineral density distribution index value, the muscle mass distribution index value, and the age of the subject corresponding to the index values and performing regression analysis on the basis of the data. Further, in a case in which the height, weight, fracture history, and the like of the subject are used to calculate the statistical value in addition to the age, it is preferable to multiply the weighting coefficients and to add the results.

In a case in which Expression (6) is used, assuming that the weighting coefficients obtained by regression analysis based on a large amount of data are "C1=2.0, C2=0.1, and C3=−0.01" and the bone mineral density distribution index value Bd, the muscle mass distribution index value, and the age Y of a certain subject are "1.0 g/cm$^2$", "20 kg", and "40 years old", respectively, the statistical value is "3.6" by the following Expression (7).

$$I = 2.0 \times 1.0 + 0.1 \times 20 + (-0.01) \times 40 = 3.6 \quad (7)$$

The evaluation value calculation unit 36 calculates a fracture risk evaluation value for evaluating the fracture risk of the subject on the basis of the statistical value. Since the relationship between the statistical value and the fracture risk evaluation value is obtained from a large amount of diagnostic data, the evaluation value calculation unit 36 calculates the fracture risk evaluation value using the relationship. The relationship between the statistical value and the fracture risk evaluation value is stored in the LUT.

Figure 9:
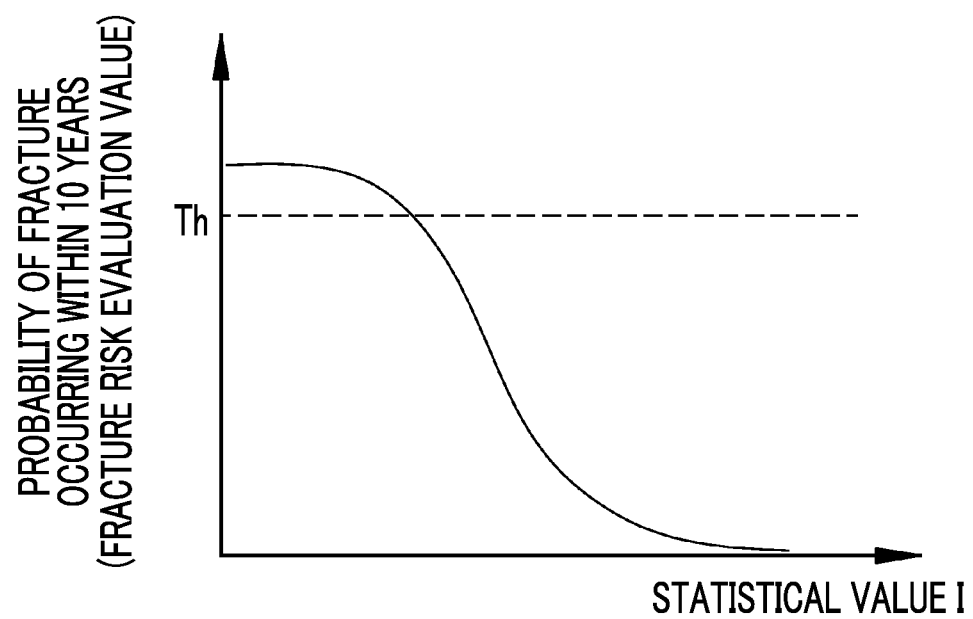
FIG. 9 is a graph illustrating a relationship between a statistical value and the probability of fracture occurring within 10 years.

An example of the fracture risk evaluation value is the probability of fracture occurring within 10 years from the diagnosis of the subject (the capture of the images of the subject by the first and second radiation detectors 15 and 16). Then, in a case in which Expression (6) is used to calculate the statistical value I and the weighting coefficients obtained by regression analysis based on a large amount of data are "C1=2.0, C2=0.1, and C3=−0.01" as described above, the relationship between the "probability of fracture occurring within 10 years" and the "statistical value I" shows that, as the statistical value I becomes larger, the probability of fracture becomes lower as illustrated in FIG. 9.

In a case in which the fracture risk evaluation value is greater than a risk threshold value, the warning generation unit 37 issues a warning to notify the user that the fracture risk of the subject is high. For example, a warning is issued in a case in which the fracture risk evaluation value is "the probability of fracture occurring within 10 years" (see FIG. 9) and the probability of fracture occurring within 10 years is greater than a risk threshold value Th. As a warning method, a warning sound may be emitted from a speaker (not illustrated) connected to the computer 12 in addition to displaying a warning screen on the display unit 18.

The display control unit 38 displays various kinds of information related to the subject H on the display unit 18. In a case in which the fracture risk evaluation value is calculated as described above, it is preferable that the display control unit 38 displays the fracture risk evaluation value as various kinds of information on the display unit 18. In this case, the fracture risk evaluation value may be displayed so as to be superimposed on the bone part image Gb, the soft part image Gs, or a composite image Gc of the soft part image Gs and the bone part image Gb.

Figure 10:
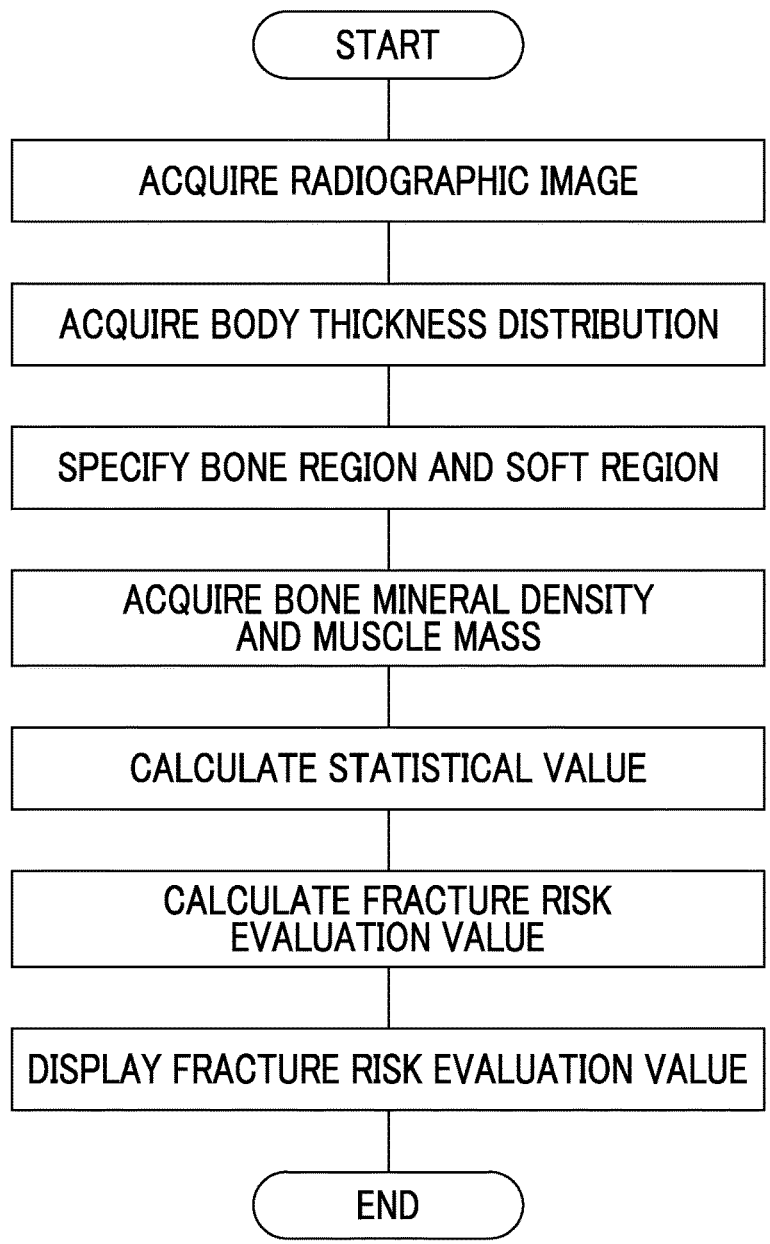
FIG. 10 is a flowchart illustrating a series of flows of the invention.

Next, a process performed in this embodiment will be described with reference to a flowchart illustrated in FIG. 10. The image acquisition unit 31 acquires the radiographic images obtained by capturing the images of the subject H irradiated with X-rays. It is preferable to acquire the first and second radiographic images G1 and G2 having different energy distributions as the radiographic images.

The body thickness distribution acquisition unit 32 acquires the body thickness distribution of the subject H. It is preferable to acquire the SID and the SOD and to subtract the SOD from the SID to acquire the body thickness distribution as a method for acquiring the body thickness distribution. Then, the region specification unit 33 specifies a bone region and a soft region included in the subject H from the radiographic images. In a case in which the first and second radiographic images G1 and G2 are acquired as the radiographic images, it is preferable to specify the bone region using energy subtraction for the first and second radiographic images G1 and G2 (Expression (1)). In addition, it is preferable to specify the soft region using energy subtraction for the first and second radiographic images G1 and G2 (Expression (2)).

Then, the subject information acquisition unit 34 calculates the bone mineral density of the bone region on the basis of the body thickness distribution, the pixel value of the bone region, and the imaging conditions in a case in which the body thickness distribution and the first and second radiographic images G1 and G2 are acquired. Further, the subject information acquisition unit 34 calculates the muscle mass of the soft region on the basis of the body thickness distribution and the pixel value of the soft region. The statistical value calculation unit 35 calculates a statistical value related to the subject on the basis of the calculated bone mineral density and muscle mass. The evaluation value calculation unit 36 calculates a fracture risk evaluation value on the basis of the statistical value. Then, the display control unit 38 displays the fracture risk evaluation value on the display unit 18.

Figure 11:
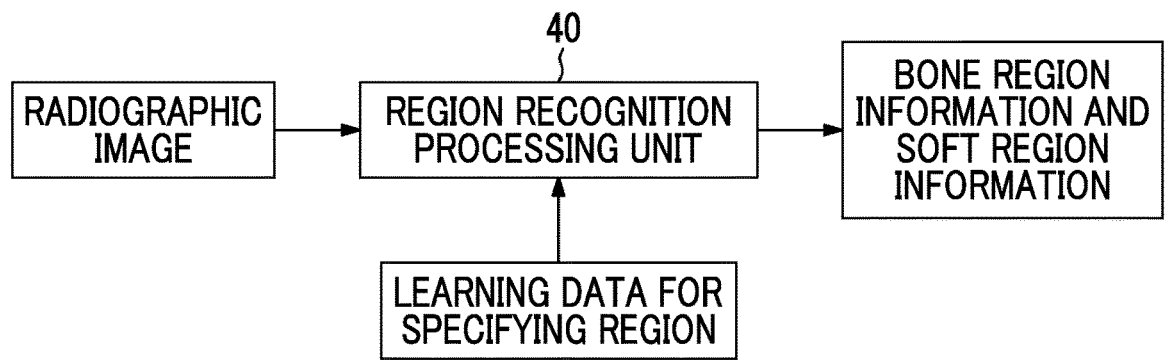
FIG. 11 is a diagram illustrating a region recognition processing unit.

Further, in the above-described embodiment, the bone region and the soft region are specified by energy subtraction for the first and second radiographic images G1 and G2 having different energy distributions. However, the bone region and the soft region may be specified by other methods. For example, as illustrated in FIG. 11, the region recognition processing unit 40 may perform a recognition process for specifying a region on one radiographic image having specific energy to specify the bone region and the soft region (the output of information related to the bone region (bone region information) and information related to the soft region (soft region information) from the region recognition processing unit 40).

In this case, it is preferable that the region recognition processing unit 40 is trained by a machine learning process, such as deep learning, using learning data for specifying a region. For example, it is preferable to use a radiographic image in which the bone region is specified by first hatching and the soft region is specified by second hatching (having a hatching aspect (for example, an angle or a scale) different from that of the first hatching) as the learning data for specifying a region.

Further, a filtering process for specifying a region may be performed on one radiographic image to specify the bone region or the soft region. For example, in a case in which there is a specific spatial frequency peculiar to a soft region, it is preferable to specify the soft region using a frequency filtering process that extracts a specific spatial frequency range. Alternatively, in a case in which the soft region has many low-frequency regions and it is difficult to specify the soft region using a frequency filtering process for extracting a soft region, the soft region may be specified by performing a frequency filtering process for extracting a bone region with a higher frequency than the soft region on a radiographic image and subtracting the radiographic image subjected to the frequency filtering process from the original radiographic image.

Further, in the above-described embodiment, the first and second radiographic images G1 and G2 are acquired by the one-shot energy subtraction. However, the first and second radiographic images G1 and G2 may be acquired by a two-shot method that irradiates the subject with radiation having different energy distributions at different timings and detects the radiation with one specific radiation detector. In the two-shot method, any one of the imaging conditions in a case in which the first radiographic image G1 is acquired or the imaging conditions in a case in which the second radiographic image G2 is acquired may be used. Further, in the two-shot method, the position of the subject H included in the first and second radiographic images G1 and G2 is likely to be shifted by the body movement of the subject H. Therefore, it is preferable to align the subject in the first radiographic image G1 and the second radiographic image G2.

For example, a plurality of first band images and a plurality of second band images indicating structures having different frequency bands are generated for each of first and second radiographic images G1 and G2, and the amount of positional deviation between the corresponding positions in the first band image and the second band image of the corresponding frequency band is acquired. Then, the registration between the first radiographic image G1 and the second radiographic image G2 is performed on the basis of the amount of positional deviation.

EXPLANATION OF REFERENCES

10: imaging apparatus
12: computer
13: X-ray source
15: first radiation detector
16: second radiation detector
17: X-ray energy conversion filter
18: display unit
19: input unit
21: CPU
22: memory
23: storage
31: image acquisition unit
32: body thickness distribution acquisition unit
33: region specification unit
34: subject information acquisition unit
34a: LUT
35: statistical value calculation unit
36: evaluation value calculation unit
37: warning generation unit
38: display control unit
40: region recognition processing unit
H: subject
G1: first radiographic image
G2: second radiographic image
Gb: bone part image
Gs: soft part image

What is claimed is:

1. A fracture risk evaluation value acquisition device comprising:
   a processor,
   wherein the processor acquires a radiographic image obtained by capturing an image of a subject including a bone part and a soft part, specifies a bone region indicating a region of the bone part and a soft region indicating a region of the soft part from the radiographic image, calculates a bone mineral density in the bone region and a muscle mass in the soft region for each pixel on the basis of the radiographic image, calculates a statistical value related to the subject on the basis of the bone mineral density and the muscle mass, and calculates a fracture risk evaluation value for evaluating a fracture risk of the subject on the basis of the statistical value.

2. The fracture risk evaluation value acquisition device according to claim 1,
   wherein the processor calculates the statistical value on the basis of a bone mineral density distribution index value related to a spatial distribution of the bone mineral density and a muscle mass distribution index value related to a spatial distribution of the muscle mass.

3. The fracture risk evaluation value acquisition device according to claim 2,
   wherein the bone mineral density distribution index value is any one of a value of the bone mineral density per unit area or an average value, an intermediate value, a maximum value, or a minimum value of the bone mineral density, and
   the muscle mass distribution index value is any one of an average value, an intermediate value, a maximum value, or a minimum value of the muscle mass.

4. The fracture risk evaluation value acquisition device according to claim 1,
   wherein the processor calculates the statistical value on the basis of at least one of a height, a weight, an age, or a fracture history of the subject in addition to the bone mineral density and the muscle mass.

5. The fracture risk evaluation value acquisition device according to claim 1,
wherein the processor issues a warning in a case in which the fracture risk evaluation value is greater than a risk threshold value.

6. The fracture risk evaluation value acquisition device according to claim 1,
wherein the processor calculates the bone mineral density on the basis of a body thickness distribution of the subject, a pixel value of the bone region, and imaging conditions in a case in which the body thickness distribution and the radiographic image are acquired.

7. The fracture risk evaluation value acquisition device according to claim 6,
wherein the processor calculates the bone mineral density by multiplying the pixel value of the bone region by a conversion coefficient based on the body thickness distribution and the imaging conditions.

8. The fracture risk evaluation value acquisition device according to claim 1,
wherein the processor calculates the muscle mass for each pixel, using a body thickness distribution of the subject and a pixel value of the soft region.

9. The fracture risk evaluation value acquisition device according to claim 8,
wherein the processor calculates the muscle mass on the basis of a predetermined specific relationship between the body thickness distribution and the pixel value of the soft region.

10. The fracture risk evaluation value acquisition device according to claim 9,
wherein the specific relationship changes depending on imaging conditions at a timing when the images of the subject are captured.

11. A method for operating a fracture risk evaluation value acquisition device,
the method comprising processor implemented steps of:
acquiring a radiographic image obtained by capturing an image of a subject including a bone part and a soft part;
specifying a bone region indicating a region of the bone part and a soft region indicating a region of the soft part from the radiographic image;
calculating a bone mineral density in the bone region and a muscle mass in the soft region for each pixel on the basis of the radiographic image;
calculating a statistical value related to the subject on the basis of the bone mineral density and the muscle mass; and
calculating a fracture risk evaluation value for evaluating a fracture risk of the subject on the basis of the statistical value.

12. A non-transitory computer readable medium for storing a computer-executable program for acquiring fracture risk evaluation value, the computer-executable program causing a computer to perform steps of:
acquiring a radiographic image obtained by capturing an image of a subject including a bone part and a soft part;
specifying a bone region indicating a region of the bone part and a soft region indicating a region of the soft part from the radiographic image;
calculating a bone mineral density in the bone region and a muscle mass in the soft region for each pixel on the basis of the radiographic image;
calculating a statistical value related to the subject on the basis of the bone mineral density and the muscle mass; and
calculating a fracture risk evaluation value for evaluating a fracture risk of the subject on the basis of the statistical value.

* * * * *